United States Patent
Schönhofer et al.

(12) 
(10) Patent No.: US 6,307,032 B1
(45) Date of Patent: Oct. 23, 2001

(54) HIGHLY PURIFIED FACTOR VIII COMPLEX

(75) Inventors: Wolfgang Schönhofer, Pölten; Johann Eibl, Vienna; Alfred Weber, Vienna; Yendra Linnau, Vienna, all of (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/171,121

(22) PCT Filed: Apr. 9, 1997

(86) PCT No.: PCT/AT97/00069

§ 371 Date: Nov. 18, 1998

§ 102(e) Date: Nov. 18, 1998

(87) PCT Pub. No.: WO97/39033

PCT Pub. Date: Oct. 23, 1997

(30) Foreign Application Priority Data

Apr. 12, 1996 (AT) .................................... 667/96

(51) Int. Cl.[7] .............. C07K 1/00; C07K 14/00; C07K 17/00; A61K 38/00
(52) U.S. Cl. .............. 530/413; 530/412; 530/383; 514/12; 514/802; 514/834
(58) Field of Search ................. 530/412, 413, 530/383; 514/12, 802, 834

(56) References Cited

FOREIGN PATENT DOCUMENTS

| | | |
|---|---|---|
| 0281089A2 | 9/1988 | (EP) . |
| 0416983A1 | 3/1991 | (EP) . |
| 01144991 | 7/1989 | (JP) . |
| WO86/01718 | 3/1986 | (WO) . |

OTHER PUBLICATIONS

Zhou et al. Purification of Factor VIII/von Willebrand Factor from Human Plasma on Immobilized Lentil Lectin. Protein Expression and Purification 5: 138–143, 1994.*
Burnouf et al. Chromatographic preparation of a Therapeutic Highly Purified von Willebrand Factor Concentrate from Human Cryoprecipitate. Vox Sang. 62(1): 1–11, 1992.*
Newman et al. Large Scale Preparation of von Willebrand Factor by Affinity Chromatography (abstract). Thromb. Haemostas 58: 356, 1987.*
Hrinda et al. Monoclonal Antibody Affinity Purifications of Plasma Proteins Removes Viral Contaminants. Colloq. INSERM 175(Biotechnol. Proteines Plasma): 413–417, 1989.*
Ramasamy et al. Biological Activity of von Willebrand factor during the manufacture of therapeutic factor VIII concentratesas determined by the collagen–binding assay. (1998) Biologicals, vol. 26, pp. 155–166.*
Hornsey et al., Thrombosis and Haemostasis 1(57): 102–105 (1987).
Koops et al., Thrombosis Research 74(4): 347–354 (1994).
R. Weinstein, Annals of Clinical and Laboratory Science, 19(2): 84–91 (1989).

* cited by examiner

*Primary Examiner*—Karen Cochrane Carlson
*Assistant Examiner*—Holly Schnizer
(74) *Attorney, Agent, or Firm*—Heller Ehrman White & McAuliffe

(57) ABSTRACT

There is disclosed a highly purified complex comprising the components factor VIII and vWF having a specific activity of at least 70, preferably 100 to 300 U factor VIII:C/mg, a stable pharmaceutical preparation containing this complex as well as a method of producing the same.

29 Claims, No Drawings

HIGHLY PURIFIED FACTOR VIII COMPLEX

The present invention relates to a highly purified complex consisting of the components factor VIII (factor VIII:C or FVIII) and von Willbrand factor (vWF), a stable pharmaceutical preparation containing the highly purified complex as well as a method of preparing a highly purified factor VIII:C/vWF-complex.

Von Willebrand factor is a multimeric glycoprotein encoded by a gene on chromosome 12 and circulating in plasma at concentrations of from 5 to 10 μg/ml freely and as non-covalent complex with coagulation factor VIII, the protein which is encoded by a gene on chromosome 10 and which is impaired or is missing, respectively, in hemophilia A.

Among the two most important functions of vWF in haemostasis are:

1) the adhesion of the thrombocytes to an injured endothelium, vWF binding to the injured sub-endothelium and enabling a bridge between this surface and the platelets as well as an aggregation of the platelets among themselves. The first interaction between thrombocytes and sub-endothelium is effected via the glycoprotein Ib of the thrombocyte membrane and the collagen fibres of the injured endothelium. vWF binds to these two proteins and thus mediates the formation of a first layer of thrombocytes. Further cross-linking of the platelets among themselves is mediated by vWF by its binding to the glycoprotein complex IIb/IIIa. For these tasks of primary haemostasis, mainly the large multimers are responsible (Eller; Lab. Med. (1994); 18: 168–176).

2) by its binding site for FVIII, vWF also influences plasmatic coagulation. FVIII is present in plasma almost exclusively in a non-covalent complex with vWF, approximately every tenth vWF molecule carrying an FVIII molecule. Primarily dimers and small multimers are used as carriers. By this complexing with vWF, FVIII is protected against an increased proteolytic inactivation (e.g. by activated protein C).

Furthermore, FVIII is potentiated by complex formation in respect of its cofactor activity in the intrinsic coagulation (Eller; Lab. Med. (1994); 18: 168–176).

vWF is formed in the vascular endothelial cells, which are the main source of this plasma protein, by constitutive or stimulated liberation, but it is also synthetized in a smaller portion by the megakariocytes. (PNAS 92 (1995), 2428–2432).

The primary product of translation is comprised of 2813 amino acids. After splitting off the signal peptide (22 amino acids), dimerisation takes place. Further processing is effected in the Golgi apparatus, the dimers polymerizing under splitting off of the propeptide (741 amino acids). The propeptide plays an important role in the further linking of the dimers, where it catalyses the formation of disulfide bridges at the amino-terminal end. Thus, differently sized oligomers ranging in size from a dimer of 500,000 daltons to large multimers of up to 20 million daltons are developed. In addition to the proteolytic procedures, vWF is subject to other post-translational modifications, including glycosylation and sulfatizing. (Mancuso et al.; Hämastaseologie (1989); 9: 122–129).

Thus, due to the complexity of the biosynthesis, there is a large number of the most varying vWF molecules having the most varying tasks and properties.

As a consequence, von Willebrand factor may exhibit quite different binding activities to its natural binding partners. In particular it has been shown that the bindings of various vWF molecules to glycoprotein Ib, to collagen, to heparin, to glycoprotein IIb/IIIa-complex, to factor VIII and to the sub-endothelium may differ in strength.

This means, however, that each vWF preparation is composed of a mixture of these different vWF proteins or vWF aggregates, respectively, and thus will be heterogenous in terms of its properties, such as its essential binding strength to factor VIII.

The occurrence of various forms of vWF is also the cause of the complex and different phenotypes in the pathophysiology of von Willebrand Disease which, in certain cases, is due to an underproduction and in other cases to an overproduction of von Willebrand factor. Thus, e.g., an overproduction of vWF leads to an increased thrombosis tendency, whereas an undersupply of vWF results in an increased bleeding tendency or in increased bleeding times; this, however, is not always so, for it is decisive in which form von Willbrand factor is over- or underproduced.

To differentiate and characterize the properties of vWF and of vWF syndrome, a number of analytical methods are used.

Thus, the ristocetin cofactor activity determination is essential for diagnostical purposes. In doing so, the thrombocyte aggregation in the presence of the antibiotic ristocetin is assayed which is reduced or not present at all in patients afflicted with vWF syndrome. (Macfarlane et al.; Thrombosis et Diathesis Haemorrhagica 1775; 34: 306–308).

Moreover, the collagen binding activity of vWF can be used for differentiating the vWF syndrome (Thomas et al.; Hämastaseologie (1994); 14: 133–139).

The binding dissociation constant between vWF and FVIII can be determined according to the method of Vlot et al. (Blood 83 (11) (1995); 3150–3157).

The molecular structure of vWF is determined by analysis of the multimer structure by means of SDS electrophoresis in 1.2% agarose gels (Ruggeri et al.; Blood (1981); 57: 1140–1143).

To determine the total amount of vWF antigen, various commercially available ELISA test kits are used.

The preparation of an optimal FVIII/vWF complex should aim at providing a stable product which, above all, is free from undesired accompanying proteins, since any unnecessary protein load harbors the risk of undesired side effects.

Thus, any concentration of vWF which is not necessary for stabilizing FVIII is a load on the hemophiliac.

In the course of methods employed for producing von Willebrand preparations, in particular from plasma pools, hitherto it has not been possible to eliminate the risk of a heterogenous composition due to the various forms of von Willebrand factor present; in the prior art it has not been possible so far to obtain a vWF preparation having uniform properties, e.g. with regard to its binding activity to a certain ligand.

It had been known to purify factor VIII complex by various anti-vWF-monoclonal antibodies both from plasma and also from cryoprecipitate (Thromb. Haemostas. 57 (1987), 102–105). In doing so, also the stability of the FVIII/vWF complex in various buffers at pH 6.5 was tested, among them buffers containing glycols, amino acids, chaotropic substances, amines, other salts or organic solvents and/or detergents. The addition of lysin to buffer solutions containing chaotropic substances at high concentrations, such as, e.g., 3M urea, resulted in a protection of factor VIII:C/vWF:Ag relative to denaturing effects. The activities of factor VIII:C and of vWF R.cof. after incubation with 20% v/v ethylene glycol+1 M KJ amounted, e.g., to 72% and 48%, respectively, after treatment with 3M urea to 88% and 77%, respectively.

The specific activity of factor VIII:C in an end product, eluted with 1 M KJ+1 M lysin+20 mM imidazole+5 mM $CaCl_2$, pH 6.5, was 45 I.U./mg total protein, that of vWF was 60 I.U./mg.

It has also been reported to chromatographically purify factor VIII/vWF-complex from cryoprecipitate after adsorption on $Al(OH)_3$ and carrying out a virus inactivation measure by using anti-vWF monoclonal antibodies (Biotechnol. Blood Prot. 227 (1993), 109–114). Elution of the adsorbed complex was effected at pH 6.5 by the addition of the chaotropic agent KJ (1 M). The ratio factor VIII:C/vWF:AG was 0.8, the specific activity of factor VIII:C was 38 I.U./mg.

Finally, it has been known from EP-0 295 645-A2 to purify factor VIII complex from heterogenous biological liquids by means of affinity chromatography, using specific peptides directed against vWF. In doing so, the complex was eluted using pH gradients or buffers of high ionic strength (cf. Example 5 of EP-0 295 645-A2).

In EP 0 416 983 A1, a preparation with factor VIII/vWF-complex is described which was prepared by anion exchange chromatography. According to WO 86/01718 A1, a factor VIII/vWF-complex preparation was obtained by chromatography on a monoclonal antibody.

What is common to all these factor VIII/vWF-complexes of the prior art is that they could not provide a preparation homogenous in terms of vWF, as regards its binding relative to factor VIII:C, despite a high enrichment and purification of the preparations, and thus there did not exist a native factor VIII/vWF-complex of high specific activity.

Thus, the present invention has as its object to provide a factor VIII/vWF-preparation comprising a factor VIII/vWF-complex which has a uniform structure as regards the binding properties of vWF relative to factor VIII, and which thus is particularly well tolerated or stable, respectively.

According to the invention, this object is achieved by a preparation comprising a highly purified complex comprised of the components factor VIII and von Willebrand factor with a specific activity of at least 70, preferably 100 to 300 U factor VIII:C/mg, which is obtainable by purifying a starting material comprising factor VIII:C and vWF by means of affinity chromatography, the complex of factor VIII:C and vWF as well as the non-complexed factor VIII:C and vWF, respectively, being eluted fractionally. Non-complexed, i.e. excessive, factor VIII:C and von Willebrand factor, respectively, are separated by immunoaffinity chromatography, in particular by the fractional elution, in which the complexed and the non-complexed factor are obtained in separate fractions.

By the inventive separating step of non-complexed factor VIII:C and von Willebrand factor, respectively, particularly von Willebrand factor molecules having an impaired affinity to factor VIII are purposefully separated, and for the first time a homogenous, native factor VIII/vWF-complex is obtained which contains a fraction of vWF that is defined as regards its affinity to factor VIII.

Surprisingly, the complex according to the invention is stable in a chaotropic environment during immunoaffinity chromatography. Even in a medium having a conductivity of up to 30 mS, preferably up to 40 mS, a dissociation of the complex could not be found. Thus, the stable complex of factor VIII and vWF from the anti-vWF column can be eluted and recovered even at a relatively high ionic strength corresponding to a 2- to 3-fold isotonic solution.

In the complex according to the invention, the vWF preferably has a collagen binding activity in the range of from 0.2 to 0.6, based on the vWF antigen (plasma unit/plasma unit).

The complex according to the invention preferably is obtainable by purifying a starting material containing the two components, the complex as well as the separate factor VIII:C or vWF, respectively, being eluted from the immunoaffinity carrier in fractions.

The eluting agents may also contain relatively high concentrations of chaotropic substances or of chaotropically active salts, since, preferably, the immunoaffinity chromatography is carried out on antibodies which retain their affinity or avidity to factor VIII or vWF even under stringent conditions, the factor VIII/vWF-complex obtained remaining stable even under these conditions.

Antibodies are chosen, e.g., which bind the antigen without adversely affecting the binding properties up to 1 M NaSCN or 0.5 M guanidinium hydrochloride, or even up to a 100% saturation with ammonium sulfate. 50% of the antigen are each still bound up to 1.5 M NaSCN or 0.75 M guanidinium hydrochloride, respectively, 80% ethylene glycol or 0.75 M urea. The antibodies used for the immunoaffinity chromatography preferably are strong antibodies which, in a binding test, bind to the immobilized antigen even from diluted solutions of 30 ng/ml at the most, preferably 15 ng/ml at the most, corresponding to an antibody/antigen ratio of 1:5 to 1:20.

Due to the excellent properties of the complex according to the invention in terms of its homogeneity, in particular with a view to the factor VIII binding properties of the vWF contained, it is particularly well suited for the production of pharmaceutical preparations for administering factor VIII and/or vWF. It has been shown that the complex according to the invention can be obtained in a concentration which is at least 5,000-fold, preferably 7,100- to 21,400-fold, enriched over plasma. A particular embodiment of the present invention thus is a stable pharmaceutical preparation comprising the highly purified complex of the invention at a concentration which is at least 5,000-fold, preferably 7,100- to 21,400-fold, enriched over plasma, the complex having a high complex binding strength and being substantially free from non-complexed vWF and factor VIII:C, respectively. In this way it is ensured that no excessive vWF or other proteins are a load on the patient, while the physiological activity of the factor VIII/vWF-complex is maintained. The preparation according to the invention is also characterized by its excellent physiological acceptance.

Its freedom from non-complexed vWF and/or factor VIII:C, respectively, means that less than 5%, preferably less than 1%, of free vWF or factor VIII:C, based on the total protein content, can be found in the pharmaceutical preparation. Particularly preferred are preparations in which no non-complexed vWF:Ag or factor VIII:C, respectively, can be detected.

The detection of non-complexed vWF or factor VIII, respectively, is effected by re-chromatography of the complex of the invention on immunoaffinity material, this material being loaded with a certain amount of free vWF or of factor VIII, respectively, the complex being adsorbed again and eluted in the manner described before. The material obtained after re-chromatography contains the same ratio of factor VIII:C to vWF:Ag as the starting material and thus does not exhibit any relative losses. A further test for detecting non-complex-bound factor VIII and vWF is the binding of the complex to immobilized factor VIII:C antibodies or vWF antibodies, no substantial portion, i.e. less than 5%, of non-bound vWF or factor VIII:C, respectively, being detectable after adsorption.

The pharmaceutical preparation according to the invention is characterized by its high reliability as regards its range of action, the risk of a degradation or of activation of factor VIII, respectively, being remarkably reduced by the small portion of free factor VIII:C or of easily dissociable factor VIII:C, respectively, as compared to known factor VIII:C/vWF-complex preparations.

It goes without saying that the pharmaceutical preparation comprising the complex of the invention may include suitable pharmaceutically active ingredients, buffers, auxiliary agents or additives which are used for factor VIII/vWF preparations. Because of the excellent stability of the factor VIII/vWF-complex, the latter may be processed into a stable pharmaceutical preparation without any further use of common stabilizers, such as albumin, sugar, in particular trehalose or sucrose.

Also in solution at a neutral pH, the pharmaceutical preparation according to the invention is sufficiently stable to be provided as a liquid preparation of a liquid-deep-frozen preparation. Upon reconstitution of a respective lyophilized preparation, also an about unchanged composition of the complex can be shown.

The dose to be administered or concentration, respectively, of the complex in the preparation can also be determined easily by the skilled artisan on the basis of prior art administering regimens for factor VIII/vWF preparations.

Factor VIII and/or vWF may be contained in the preparation according to the invention as native protein, or as derivative thereof, e.g. as a protein mutated by deletion, substitution or insertion, or as a chemical derivative or fragment, respectively, insofar as the high binding affinity of factor VIII to vWF is retained in the complex.

Subject matter of the present invention is also a method by which the complex according to the invention can be prepared, which comprises purifying the starting material containing factor VIII:C and vWF by means of immunoaffinity chromatography, the complex of factor VIII:C and vWF as well as the non-complexed factor VIII:C and vWF, respectively, being eluted fractionally. By the purposeful fractional elution of the non-complexed factors from the complex it has for the first time been possible to obtain a von Willebrand factor preparation or a factor VIII/vWF-complex, respectively, that is uniform in terms of a specific binding strength.

Preferably, antibodies directed against vWF are used for immunoaffinity chromatography. In this manner, the purification method which is substantially directed at fractionating different vWF molecules or vWF units can be even better directed at the different nature of the von Willebrand molecule.

According to a particular embodiment of the method according to the invention, monoclonal antibodies are used as the antibodies. In terms of homogeneity, they are to be preferred to a polyclonal antiserum.

A preferred elution buffer for the inventive complex during affinity chromatography is a buffer comprising a thiocyanate and/or an ammonium salt, preferably at a concentration not exceeding 2 M, most preferred in the range of from 0.05 M to 1.5 M. This first elution buffer may preferably contain ethylene glycol, glycerol or a polyalkylene glycol.

Non-complexed factor VIII:C or vWF, respectively, preferably are eluted with a buffer containing a chaotropic agent, in particular thiocyanate, and/or ammonium salt, and/or alkaline salts and/or ethylene glycol, glycerol or a polyalkylene glycol and also are recovered as homogenous preparations. In doing so, the buffer has a concentration or conductivity, respectively, which is increased over the first elution buffer, in particular a concentration or conductivity, respectively, which is more than 20%, preferably more than 50% to 100%, higher.

A further subject matter of the present invention thus consists in a von Willebrand preparation having a reduced binding or complexing capacity relative to factor VIII:C and which can be recovered by the present method.

The highly purified complex, but also the inventive non-complexed factor VIII:C or vWF preparations, respectively, may optionally be further purified by further chromatographic steps, preferably ion exchange chromatography, gel filtration, hydrophobic chromatography, affinity chromatography, in particular on immobilized heparin, or metal ion chelate chromatography, and be processed in a known and suitable manner into pharmaceutical and also diagnostic preparations.

For producing pharmaceutical preparations as a rule it is necessary to provide a measure for inactivating or depleting viruses, preferably a heat treatment and/or a physical or chemical treatment. Suitable methods have been described in EP-0 159 311, EP 0 519 901 as well as WO 94/13329. Since the complex of the invention has a high stability, this virus inactivation measure preferably is performed on the highly purified complex.

According to a preferred embodiment of the method of the invention, the starting material is selected from the group consisting of plasma, a plasma fraction, such as, e.g., cryoprecipitate or an alcohol precipitate, a cell culture supernatant and a pharmaceutical preparation.

The invention will be explained in more detail by way of the following examples to which, however, it shall not be restricted.

EXAMPLE 1

(At Present Considered by Applicant to be the Best Mode of Carrying Out the Claimed Invention)

500 g of cryoprecipitate are dissolved 1+4 in dissolution buffer at 30° C. Subsequently, the solution is clarified via a 0.45 μm filter (e.g. Millipore Durapore). A column filled with 0.5 l anti-vWF gel (IMMUNOTECH, France) is prepared with approximately 10 column volumes (CV) equibuffer, and the clarified cryoprecipitate solution is applied thereto at 0.5 cm/min. Thereafter, adversely affecting impurities are washed out with 5 to 10 CV of equibuffer (possibly with an increased NaCl concentration >250 mM) at a flow rate of 1 cm/min. Factor VIII/vWF-complex is then eluted with elution buffer 1 an approximate ratio of 1:1. Elution with elution buffer 2 yields vWF which is almost completely free from factor VIII. The second elution step simultaneously serves for purifying the column to allow for immediate equilibration thereafter.

| | | |
|---|---|---|
| Dissolution buffer: | 7.5 mM Tris | |
| | 60 mM NaCl | |
| | 100 mM lysin | |
| | 100 mM Na acetate | pH 6.8 |
| | 25 U/ml heparin | |
| Equibuffer: | 10 mM Tris | |
| | 100 mM NaCl | |
| | 100 mM lysin | |
| | 3.25 mM CaCl$_2$ | pH 6.8 |
| Elution buffer 1: | 10 mM Tris | |
| | 100 mM glycin | |
| | 250 mM NaCl | |
| | 300 mM AMS | |
| | 3 mM CaCl$_2$ | |
| | 40% ethylene glycol | pH 6.5 |
| Elution buffer 2: | 10 mM Tris | |
| | 100 mM glycin | |
| | 1.25 M NaCl | |
| | 1.25 mM NaSCN | |
| | 3 mM CaCl$_2$ | |
| | 40% ethylene glycol | pH 7.0 |

Results:

| Sample | U/ml FVIII:C | % Yield FVIII:C | U/mg FVIII:C | U/ml vWF | % Yield vWF | U/mg to vWF | FVIII:C to vWF | Collag.B. relat. to vWF |
|---|---|---|---|---|---|---|---|---|
| Start | 11.0 | 100.0% | 0.4 | 16.3 | 100.0% | 0.6 | 1:1.48 | 0.7 |
| FVIII/vWF | 12.7 | 50.9% | 133.7 | 14.7 | 39.8% | | 1:1.16 | 0.3 |
| vWF | 0.2 | 0.5% | | 23.4 | 37.2% | 236.4 | | 0.7 |

EXAMPLE 2

1 l of fresh frozen plasma is thawed at T>25° C. and subsequently diluted 1+2 with equibuffer. The solution is clarified through a 0.45 μm filter. A column filled with 50 ml anti-vWF gel (IMMUNOTECH) is prepared with approximately 5 CV of equibuffer, and then the clarified plasma solution is applied at a flow rate of 1 cm/min. The undesired impurities are washed out with 10 to 20 CV of equibuffer+ 250 mM NaCl. The first elution yields factor VIII/vWF-complex; the second elution vWF free from factor VIII activity. Then the column may immediately be equilibrated again.

| | | |
|---|---|---|
| Equibuffer: | 5 g/l Na citrate | |
| | 2 U/ml heparin | pH 7.0 |
| Elution buffer 1: | 5 g/l Na citrate | |
| | 30 g/l AMS | |
| | 20 g/l NaSCN | |
| | 75 g/l histidine | |
| | 5 g/l NaCl | |
| | 0.4 g/l CaCl$_2$ | pH 7.0 |
| Elution buffer 2: | 5 g/l Na citrate | |
| | 50 g/l AMS | |
| | 50 g/l NaSCN | |
| | 75 g/l histidine | |
| | 25 g/l NaCl | |
| | 0.4 g/l CaCl$_2$ | pH 7.0 |

Results:

| Sample | U/ml FVIII:C | % Yield FVIII:C | U/mg FVIII | U/ml vWF | % Yield vWF | U/mg vWF | FVIII:C to vWF | Collag.B. relat. to vWF |
|---|---|---|---|---|---|---|---|---|
| Start | 0.3 | 100.0% | 0.01 | 0.3 | 100.0% | 0.01 | 1:1 | 1.0 |
| FVIII/vWF | 2.4 | 33.3% | 42.86 | 1.8 | 24.3% | | 1:0.75 | 0.5 |
| vWF | 0.0 | 0.2% | | 4.5 | 76.0% | 112.50 | | 0.8 |

What is claimed is:

1. A method of fractionating a composition comprising factor VIII:C and von Willebrand factor (vWF), comprising contacting the composition with an immunoaffinity chromatography material;

eluting factor VIII/vWF-complex with a first elution buffer; and then eluting non-complexed factor VIII:C or vWF with a second elution buffer, wherein the second elution buffer has a concentration or conductivity that is at least 20% higher than the first elution buffer, and wherein the collagen binding activity of the VIII/vWF complex is 0.2 to 0.6 of the collagen binding activity of vWF antigen.

2. The method according to claim 1, wherein the immunoaffinity chromatography material comprises anti-vWF antibodies.

3. The method according to claim 2, wherein the antibodies are monoclonal antibodies.

4. The method according to claim 2, wherein the antibodies have a high affinity to vWF and are able to bind vWF in a medium containing 1 M thiocyanate.

5. The method according to claim 1, wherein the first elution buffer comprises at least one salt selected from the group consisting of a thiocyanate salt and an ammonium salt.

6. The method according to claim 5, wherein the first buffer has a concentration of the salt of no more than 2M.

7. The method according to claim 5, wherein the first buffer has a concentration of the salt of no more than 0.05M to 1.5M.

8. The method according to claim 1, wherein the first buffer comprises one selected from the group consisting of ethylene glycol, glycerol and polyalkylene glycol.

9. The method according to claim 1, wherein the second elution buffer contains at least one selected from the group consisting of a chaotropic agent, an ammonium salt, an alkaline salt, and a glycol.

10. The method according to claim 9, wherein said chaotropic agent is thiocyanate.

11. The method according to claim 9, wherein the glycol is selected from the group consisting of ethylene glycol, glycerol and polyalkylene glycol.

12. The method according to claim 1, further comprising purifying the factor VIII/vWF-complex by further chromatography.

13. The method according to claim 12, wherein the further chromatography is selected from the group consisting of ion exchange chromatography, gel filtration, hydrophobic chromatography, affinity chromatography and metal ion chelate chromatography.

14. The method according to claim 1, further comprising inactivating or depleting viruses.

15. The method according to claim 14, wherein the inactivating or depleting of viruses comprises a heat treatment.

16. The method according to claim 14, wherein the inactivating or depleting of viruses is performed on the factor VIII/vWF-complex.

17. The method according to claim 1, wherein the starting material is selected from the group consisting of plasma, a plasma fraction, a cell culture supernatant and a pharmaceutical preparation.

18. A preparation comprising a highly purified complex of factor VIII:C and von Willebrand factor (vWF), wherein the complex can be obtained by contacting a starting material containing the factor VIII:C and vWF with an immunoaffinity chromatography material and eluting factor VIII/vWF-complex with an elution buffer, wherein the preparation is free from non-complexed vWF and factor VIII:C and has a specific activity of at least 70 U of factor VIII:C/mg, and wherein the collagen binding activity of the VIII/vWF complex is 0.2 to 0.6 of the collagen binding activity of vWF antigen.

19. The preparation according to claim 18, wherein the specific activity is from 100 to 300 U of factor VIII:C/mg.

20. The preparation according to claim 18, wherein the complex is at least 5000-fold enriched as compared the complex content in plasma.

21. The preparation according to claim 18, wherein the complex is 7,100-fold to 21,400-fold enriched as compared to the complex content in plasma.

22. The preparation according to claim 18, wherein said preparation is formulated as a pharmaceutical preparation.

23. The preparation according to claim 18, wherein the immunoaffinity chromatography column comprises anti-vWF antibodies.

24. The preparation according to claim 23, wherein the anti-vWF antibodies are monoclonal antibodies.

25. The preparation according to claim 24, wherein the antibodies have a high affinity to vWF and are able to bind vWF in a medium containing 1 M thiocyanate.

26. The preparation according to claim 18, wherein the elution buffer contains at least one salt selected from the group consisting of a thiocyanate salt and an ammonium salt.

27. The preparation according to claim 26, wherein the buffer has a concentration of the salt of no more than 2M.

28. The preparation according to claim 26, wherein the buffer has a concentration of the salt of 0.05M to 1.5M.

29. The preparation according to claim 18, wherein the elution buffer contains at least one selected from the group consisting of ethylene glycol, glycerol and polyalkylene glycol.

* * * * *